United States Patent
Döring

(10) Patent No.: US 9,475,860 B2
(45) Date of Patent: Oct. 25, 2016

(54) PROCESS FOR OBTAINING IMMUNOGLOBULINS FROM COLOSTRAL MILK

(71) Applicant: DMK Deutsches Milchkontor GmbH, Zeven (DE)

(72) Inventor: Sven-Rainer Döring, Zeven (DE)

(73) Assignee: DMK Deutsches Milchkontor GmbH, Zeven (DE)

( * ) Notice: Subject to any disclaimer, the term of this patent is extended or adjusted under 35 U.S.C. 154(b) by 185 days.

(21) Appl. No.: 14/168,586

(22) Filed: Jan. 30, 2014

(65) Prior Publication Data

US 2014/0213774 A1    Jul. 31, 2014

(30) Foreign Application Priority Data

Jan. 31, 2013    (EP) .................... 13153472

(51) Int. Cl.
| | | |
|---|---|---|
| C07K 16/04 | (2006.01) | |
| A23C 9/142 | (2006.01) | |
| A23J 3/08 | (2006.01) | |
| A23C 9/20 | (2006.01) | |

(52) U.S. Cl.
CPC ............ *C07K 16/04* (2013.01); *A23C 9/1422* (2013.01); *A23C 9/206* (2013.01); *A23J 3/08* (2013.01)

(58) Field of Classification Search
None
See application file for complete search history.

(56) References Cited

U.S. PATENT DOCUMENTS

| | | | | |
|---|---|---|---|---|
| 2011/0130545 A1* | 6/2011 | Hensgens | ............... | C07K 16/04 530/387.1 |
| 2012/0213796 A1* | 8/2012 | Fox | ........................ | C07K 16/00 424/158.1 |

FOREIGN PATENT DOCUMENTS

| | | | | |
|---|---|---|---|---|
| NZ | WO 0103515 A1 * | 1/2001 | ........... | A23C 9/1422 |
| WO | 01/03515 A1 | 1/2001 | | |

OTHER PUBLICATIONS

Piot et al: "Preparation of serocolostrum by membrane microfiltration," Dairy Science and Technology (Le Lait) EDP Sciences, Paris, France, vol. 84, Jan. 1, 2004, pp. 333-341.
Elfstrand et al: "Immunoglobulins, growth factors and growth hormone in bovine colostrum and the effects of processing," International Diary Journal, Elsevier Applied Science, Barking, Great Britain, vol. 12, Issue 11, Jan. 1, 2002, pp. 879-887.
Carvalho et al: "Chapter 3. Applications of Membrane Technologies in the Dairy Industry," Jan. 1, 2010, Engineering Aspects of Milk and Dairy Products, Boca Raton, Florida, CRC Press, Taylor and Francis Group, pp. 33-56.
Heino: "Microfiltration in Cheese and Whey Processing," University of Helsinki, Department of Food Technology, Jan. 15, 2010, pp. 50-112.
Ollikainen et al: "Effect of Pasteurization on the distribution of bovine milk transforming growth factor-$\beta 2$ in casein and whey fractions during micro- and ultrafiltration processes," International Dairy Journal, Elsevier Applied Science, Barking, Great Britain, vol. 26, Issue 2, Apr. 9, 2012, pp. 141-146.
Gerberding et al: "Preparative ion-exchange chromatography of proteins from dairy whey," Journal of Chromatography, Elsevier Science Publishers, B.V. Netherlands, vol. 808, Issues 1-2, May 29, 1998, pp. 141-151.
Gosch et al: "Improved isolation of bioactive components of bovine colostrum using cross-flow microfiltration," International Journal of Dairy Technology, vol. 66, Jan. 21, 2013, pp. 1-7.
Wu et al: "Chapter 15. Isolation and Purification of Bioactive Proteins from Bovine Colostrum," Progress in Molecular and Environmental Bioengineering—From Analysis and Modeling to Technology Applications, Aug. 1, 2011, pp. 347-366.
Bazinet et al: "Chapter 12. Emerging Membrane Technologies and Applications for Added—Value Dairy ingredients," Membrane Technologies and Applications, Jan. 1, 2011, CRC Press, pp. 201-212.

* cited by examiner

*Primary Examiner* — Daniel E Kolker
*Assistant Examiner* — James Rogers
(74) *Attorney, Agent, or Firm* — Dilworth & Barrese, LLP

(57) ABSTRACT

Suggested is a process for obtaining immunoglobulins, wherein
(a) colostral milk from days 0 to 7 is subjected to thermal treatment, skimming the cream,
(b) the skimmed milk such obtained is subjected to sterile microfiltration thus producing a first retentate R1 which contains the casein, and a first permeate P1,
(c) the first permeate P1 is subjected to ultrafiltration thus producing a second permeate P2 which contains lactose and minerals, and a second retentate R2, in which the immunoglobulins are concentrated.

9 Claims, No Drawings

PROCESS FOR OBTAINING IMMUNOGLOBULINS FROM COLOSTRAL MILK

FIELD OF THE INVENTION

The invention generally relates to the field of pharmaceutical compositions and specifically relates to a process for obtaining immunoglobulins wherein colostral milk is subjected to combined microfiltration and ultrafiltration.

PRIOR ART

Colostral milk is the first milk given to new-born mammals, produced by the female mammary glands to optimally feed the new-born in the first days of its life. It is also referred to as foremilk, beestings, first milk and, particularly, colostral milk and contains proteins, enzymes, vitamins, minerals, growth factors, amino acids and antibodies. In this manner it supports the young mammal's strength and immune defence. Colostral milk is said to be a healthy food.

There are numerous studies on the effectiveness of colostral milk. Among others, colostral milk is said to provide a certain protection against infectious diseases (cf. Cesarone et al., Clinical and Applied Thrombosis/Hemostasis 13 (2), 130-136 (2007)) and to support both wound healing and the regeneration of damaged intestinal mucosa. Colostral milk is also used in a co-treatment of allergies, high blood pressure, diabetes mellitus and depression. To this date, however, there is no proof of effectiveness of the use in these indications yet.

Colostral milk from cows is particularly interesting as a source of raw material, specifically of immunoglobulins. However, it has been technologically reasonable to only use the milk produced within the first 24 hours up to 48 hours post partum at the longest for a separation, because later the globulin content would fall markedly in a way that concentrating it would cease to be economically reasonable.

EP 0410272 A1 (Biotest) describes the production of an immunoglobulin concentrate wherein colostral milk from the first 30 hours post partum is skimmed, pasteurised, sterilized, subjected to ultrafiltration and spray-dried. However, this process is only economic when colostral milk with a comparably high immunoglobulin content is used. The concentration process is not suitable for milk obtained only after 48 hours.

Subject matter of EP 0918464 B1 (Achenbach) is a process for the production of a decaseinated colostral milk product wherein raw colostral milk is skimmed and acidified such that the casein is kept in solution and an ultrafiltration process with a cut-off molecular weight of at least $10^6$ Dalton is performed. The colostral milk product such obtained is particularly suitable for use as an additive for pharmaceutical products, for dietary supplements, beverages, infant food, animal feed, in the form of beverages used in intensive sports for muscle cell protection or for reducing the muscle recovery phase and for the prevention and treatment of bacterial, viral and mycotic infections. This publication, however, does not relate to the concentration of immunoglobulins.

EP 0410272 A1 (Biotest) describes the production of an immunoglobulin concentrate wherein colostral milk from the first 30 hours post partum is skimmed, pasteurized, sterilized, subjected to ultrafiltration and eventually spray-dried.

Further, AT 511308 A2 (Vitalplus) discloses a process for the production of a colostral milk product which is either low in lactose or lactose-free wherein raw colostral milk is skimmed and decaseinated, and the product containing the high-molecular ingredients which is obtained after ultrafiltration is subjected to sterilisation and/or sterile filtration. The permeate from the ultrafiltration step, containing, in particular, low-molecular ingredients of raw colostral milk and lactose is subjected to lactose cleavage and, subsequently, the low molecular ingredients and the lactose cleavage products are again added to the product which contains the high molecular ingredients before or during sterilization or sterile filtration. The process, however, does not have as its object immunoglobulin concentration and obtainment.

Eventually, EP 0085005 B1 (Fromageries Bel) discloses a process for the separation of immunoglobulins from colostral milk, wherein the colostral milk is subjected to cleavage by means of electrophoresis, which subjects the fraction enriched with immunoglobulins to electrophoresis, passing the obtained first concentrated fraction through an anion exchanger in order to thus obtain a second, further concentrated fraction with immunoglobulins.

The object of the present invention has thus been to provide a process by means of which it is possible to concentrate the immunoglobulin content also in colostral milk collected in days 2 to 7 post partum, keeping the technological effort as low as possible.

DESCRIPTION OF THE INVENTION

Subject matter of the invention is a process for obtaining immunoglobulins wherein (a) colostral milk from days 0 to 7 is subjected to thermal treatment, skimming the cream, (b) the skimmed milk such obtained is subjected to sterile microfiltration thus producing a first retentate R1 which contains the casein, and a first permeate P1

(c) the first permeate P1 is subjected to ultrafiltration thus producing a second permeate P2 which contains lactose and minerals, and a second retentate R2, in which the immunoglobulins, specifically the valuable species $IgG_1$, IgA and IgM, are concentrated.

Surprisingly it was found that in this manner a fraction can be obtained which contains up to 15 % by weight immunoglobulins also when colostral milk is used which was collected within up to 7 days post partum. Said fraction can then be concentrated, preferably using ion exchangers, up to an immunoglobulin content of from 85 to 90% by weight. Subsequently, the products can be further purified and concentrated by means of drying, dialysis or ultrafiltration.

Thermal Treatment

The thermal treatment of colostral milk ("purification") is preferably performed in heat exchangers, whereby specifically plate heat exchangers have proven to be particularly suitable. There is a temperature gradient at the heat exchangers which, however, is selected such that the colostral milk is heated to a temperature of from about 70 to 80° C. and, more particularly, from about 72 to 74° C., for a residence time of a minimum of 10 and a maximum of 30 seconds, preferably, about 15 seconds.

The separation of solid non-milk particles such as, for example, somatic cells, straw particles and similar as well as the skimming of the fat content of about 4% by weight is usually carried out in a downstream component, preferably, a separator. Such components are adequately known from the state of the art. Separators by the company GEA Westfalia Separator GmbH, which allow the joint or single use of both steps (http://www.westfalia-separator.com/de/anwendungen/molkereitechnik/milch-molke.html) are widely used in the dairy industry. Corresponding components have been disclosed, for example, in DE 10036085 C1 (Westfalia) and are perfectly known to one skilled in the art. Thus no explanations are needed on carrying out these process steps, as they are understood to be part of the general specialist knowledge.

Microfiltration and Ultrafiltration

The core of the process according to the invention is the combination of microfiltration and ultrafiltration.

Microfiltration is a process for substance removal. The essential difference between microfiltration and ultrafiltration lies in the different pore sizes and the different membrane structure as well as in the materials and filter materials involved. A filtration through membranes having a pore size of <0.1 µm is usually referred to as ultrafiltration, while a filtration using pore sizes of >0.1 µm is usually referred to as microfiltration. In both cases purely physical, i.e., mechanical membrane separation methods which apply the principle of mechanical size exclusion are concerned: all particles in the fluids which are larger than the membrane pores are retained by the membrane. The driving force in both separation methods is the differential pressure between the inlet and the outlet of the filter area, which is between 0.1 and 10 bar. The filter area material may consist of— depending on the area of application—stainless steel, synthetic material, ceramic or textile fabric. Filter elements appear in different forms: candle filters, flat membranes, spiral coil membranes, bag filters and hollow fibre modules; all of them are principally suitable within the meaning of the present invention.

After thermal treatment and skimming, the skimmed milk is subjected to microfiltration, thus separating not only microorganisms, but especially the casein with the first retentate R1 such obtained. Microfiltration is preferably performed by means of membranes having a selective separation of 0.2, preferably, of 0.1 µm. This has surprisingly proven to be sufficient also before the background of purification, because the majority of thermolabile spores had been separated as a result of the thermal treatment and discharged together with the separator slime before. Combining said pore diameter and a microfiltration device which essentially consists of a spiral coil membrane, preferably, however, a ceramic membrane, simultaneously solves the problem of frequent clogging. In doing so, microfiltration may be performed "cold" or "warm", i.e., at temperatures within the range of from 5 to 70 °C. Preferably, however, microfiltration is performed at temperatures within the range of from 50 to 55° C., because denaturation is avoided under these conditions and a maximum flux and optimum permeability of the whey proteins into the permeate are allowed.

The first permeate P1 obtained during microfiltration is subjected to an ultrafiltration step. In doing so, a second permeate P2 is obtained which essentially contains lactose and minerals ("ash") and which can be processed separately. In this process, spiral coil membranes on a polymer basis are particularly suitable; other materials can also be used, in principle, however, they are usually much more expensive while they do not show a notably higher performance. Ultrafiltration is preferably performed using membranes with a selective separation of from 0.01 to 0.1 µm. Ultrafiltration can also be carried out "cold" or "warm", i.e., at temperatures within the range of from 5 to 70° C. In the case of ultrafiltration it is useful to carry out a cold filtration, i.e., at temperatures within the range of from 10 to 15° C. to avoid damaging of the whey proteins.

Separation of the Immunoglobulins

The separation of the immunoglobulins from the second retentate may be performed according to the processes known from the prior art, particularly according to a process described in EP 0085005 B1 cited above. Preferably, the second retentate is passed through a column filled with anion exchanger particles. Particularly suitable for this purpose are, for example, porous products which are marketed by Rhone-Poulenc under the name Spherosil, particularly the types QMA (exchanger which is sensitive to extreme alkaline pH), C (exchanger which is sensitive to very weakly acidic pH), S (exchanger which is sensitive to extreme acidic pH), and X OB 015 (exchanger which is sensitive to very weakly acidic pH), which are usually available on a carrier of porous silica. Also suitable, for example, is the product Trisacryl by I.B.F. The ion exchangers mentioned have the advantage that they do not change the preferred pH value at which separation is to be carried out and which is between 7 and 8. This particularly avoids the denaturation of the globulins. The separation can be performed at temperatures within the range of between 2 and 25 and, preferably, 3 and 10° C. The immunoglobulins are adsorbed on the resins, while the secreted medium is practically free of immunoglobulins. By washing the column with 1N HCl the immunoglobulins can be made soluble again and be practically completely recovered. Subsequently, the fraction thus obtained can be concentrated by drying, dialysis, ultrafiltration and similar processes up to a concentration of from 98 to 100% by weight.

EXAMPLES

Example 1

Colostral milk from days 0 to 7 having an immunoglobulin content of 3% by weight was heated in a plate heat exchanger to 72° C. for 15 s. By means of the connected separator the colostral milk such pasteurized was skimmed and solids were removed. The skimmed milk obtained was subjected to microfiltration at 50° C. by means of a ceramic membrane having a pore diameter of 0.1 µm and the casein-containing retentate R1 was separated. The permeate P1 was also subjected to ultrafiltration at 10° C. by means of a spiral coil membrane having a pore diameter of 0.04 µm. In doing so, both a second permeate P2 was obtained which contained lactose and minerals and which was processed separately, and a second retentate R2 which had an immunoglobulin content of 15% by weight.

2 l of the retentate were passed through an anion exchanger column filled with a resin of the type Spherosil QMA. The temperature was 4° C., the pH value was about 6.5, the flow rate was 300 ml/h. The medium passing through had a residual content of immunoglobulins of less than 0.5% by weight. The column was then washed with 500 ml 1N HCl. The fraction thus obtained had a protein content of 30% by weight and, in relation to the protein amount, a content of 89% by weight immunoglobulins and 11% by weight albumins. Subsequent spray-drying yielded a dry powder.

Comparison Example V1

Colostral milk from days 0 to 7 having an immunoglobulin content of 3% by weight was heated in a plate heat exchanger to 72° C. for 15 s. By means of the connected separator the colostral milk such pasteurized was skimmed and solids were removed. The skimmed milk obtained was acidified such that the casein was kept in solution and then subjected to ultrafiltration at 25° C. by means of a spiral coil membrane having a pore diameter of 0.04 µm. In doing so, both a permeate P1 was obtained which contained lactose and minerals and which was processed separately, and a retentate R1 which had an immunoglobulin content of 8% by weight.

2 l of the retentate were passed through an anion exchanger column filled with a resin of the type Spherosil QMA. The temperature was 4° C., the pH value was about 6.5, the flow rate was 300 ml/h. The medium passing through had a residual content of immunoglobulins of less than 0.5% by weight. The column was then washed with 500 ml 1N HCl. The fraction thus obtained had a protein content of 22% by weight and, in relation to the protein amount, a content of 71% by weight immunoglobulins and 29% by weight albumins. Subsequent spray-drying yielded a dry powder.

The invention claimed is:

1. A process for obtaining immunoglobulins consisting essentially of:
    (a) colostral milk from days 0 to 7 is subjected to thermal treatment, skimming the cream,
    (b) the skimmed milk such obtained is subjected at a temperature of from about 50 to about 70° C. to a sterile microfiltration thus producing a first retentate R1 which contains the casein, and a first permeate P1,
    (c) the first permeate P1 is subjected at a temperature of from about 5 to about 15° C. to ultrafiltration thus producing a second permeate P2 which contains lactose and minerals, and a second retentate R2, in which the immunoglobulins are concentrated, and
    (d) the immunoglobulins thus obtained from the second retentate are separated off from by treatment with anion exchanger.

2. The process of claim 1 wherein the colostral milk is treated at a temperature of from about 70 to about 80° C.

3. The process of claim 1, wherein the colostral milk is treated for a period from about 10 to about 30 s.

4. The process of claim 1, wherein microfiltration is performed using membranes having a selective separation of from about 0.1 to about 0.2 µm.

5. The process of claim 1, wherein microfiltration is performed by means of a ceramic membrane.

6. The process of claim 1, wherein ultrafiltration is performed using membranes having a selective separation of from about 0.01 to about 0.1 µm.

7. The process of claim 1, wherein ultrafiltration is performed by means of a spiral coil membrane.

8. The process of claim 1, wherein separation is performed by means of an anion exchanger at a temperature within the range of from about 2 to about 25° C.

9. The process of claim 1, wherein separation is performed by means of an anion exchanger at a pH value of from about 6 to about 7.

* * * * *